US00PP20043P3

(12) United States Plant Patent
Hambali

(10) Patent No.: US PP20,043 P3
(45) Date of Patent: Jun. 2, 2009

(54) ***AGLAONEMA* PLANT NAMED 'TWYAG0054'**

(50) Latin Name: *Aglaonema* hybrid
Varietal Denomination: TWYAG0054

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 35 days.

(21) Appl. No.: 11/904,080

(22) Filed: Sep. 26, 2007

(65) Prior Publication Data

US 2009/0083889 P1 Mar. 26, 2009

(51) Int. Cl.
*A01H 5/00* (2006.01)

(52) U.S. Cl. ..... Plt./376

(58) Field of Classification Search ..... Plt./376
See application file for complete search history.

*Primary Examiner*—Annette H Para
*Assistant Examiner*—Louanne C Krawczewicz Myers
(74) *Attorney, Agent, or Firm*—Jondle & Associates, P.C.

(57) ABSTRACT

A new *Aglaonema* plant particularly distinguished by having a leafy, compact and very small growth habit, medium to dark green foliage with dark grey-green areas which follow the primary veins, foliage that is marked with small coalescing yellow-green spots and blotches, areas adjacent to the primary veins that are often marked with yellow-green, areas adjacent to the midrib are variably tinged with pink and the primary veins are flushed with pink, and light pink to white spathes, is disclosed.

1 Drawing Sheet

Genus and species: *Aglaonema* hybrid.
Variety denomination: 'TWYAG0054'.

BACKGROUND OF THE NEW PLANT

The present invention comprises a new and distinct cultivar of *Aglaonema*, botanically known as *Aglaonema* hybrid and hereinafter referred to by the variety name as 'TWYAG0054'. The new variety originated from an open pollination made in Bogor, West Java, Indonesia between unknown individual plants of *Aglaonema*(species unknown). The new variety was discovered as a single plant within the progeny of the stated open pollination in a controlled environment in Bogor, West Java, Indonesia.

The new variety was created in Bogor, West Java, Indonesia and has been asexually reproduced repeatedly by vegetative cuttings and tissue culture in Apopka, Fla. for two or more generations. The present invention has been found to retain its distinctive characteristics through successive asexual propagations.

SUMMARY OF THE INVENTION

The following are the most outstanding and distinguishing characteristics of the new variety when grown under normal horticultural practices in Apopka, Fla.

1. Medium to dark green foliage with dark grey-green areas which follow the primary veins;
2. Foliage that is marked with small coalescing yellow-green spots and blotches;
3. Areas adjacent to the primary veins are often marked with yellow-green;
4. Areas adjacent to the midrib are variably tinged with pink and the primary veins are flushed with pink;
5. Leafy, compact and very small in stature; and
6. Light pink to white spathes.

DESCRIPTION OF THE PHOTOGRAPH

This new *Aglaonema* plant is illustrated by the accompanying photograph which shows the overall plant habit. The colors shown are as true as can be reasonably obtained by conventional photographic procedures.

DESCRIPTION OF THE NEW VARIETY

The following detailed description sets forth the distinctive characteristics of 'TWYAG0054'. The data which define these characteristics were collected from asexual reproductions carried out in Apopka, Fla. The plant history was taken on 12 month-old plants started from a single four-leaf rooted cutting, still in a vegetative state and grown in Apopka, Fla. Rooted cuttings were planted in 20-cm pots and grown in a greenhouse in October 2006. The plants were pinched once. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family.*—Araceae.
- *Botanical.*—*Aglaonema* hybrid.
- *Cultivar name.*—'TWYAG0054'.
- *Common.*—Chinese Evergreen.

Growth:
- *Form.*—Symmetrical; new leaves are held upright and mature leaves are held outward.
- *Growth and branching habit.*—Leafy and compact; upright, branched and very small in stature.
- *Height* (*from soil to top of leaf plane*).—17 cm to 22 cm.
- *Diameter* (*area of spread, as measured from leaf tip to leaf tip across the canopy*).—25 cm to 30 cm.

*Growth rate.*—Typical of commercial *Aglaonema* varieties.

*Vigor.*—Plants produce axillary branches and numerous leaves.

*Time to produce a finished flowering plant.*—About 12 months starting from a single 4-leaf rooted cutting with the plants pinched once in 10 cm to 20 cm pots.

*Root description.*—Abundant, fleshy and white with finer lateral branches.

*Number of divisions or clumps per year.*—About six 4-leaf cuttings per year.

*Durability of foliage to stresses.*—Foliage holds up well against damage from shipping and handling; plants are durable and have excellent indoor keeping quality.

*High temperature tolerance.*—About 104° F. for several hours without damage.

*Low temperature tolerance.*—About 55° F. for several hours without damage.

Stems:

*Number of branches per plant.*—About 12.

*Type of branching.*—Basal.

*Length* (*from soil line to junction of the newest two leaves*).—10 cm.

*Diameter* (*measured at the midpoint*).—0.80 cm.

*Internode length.*—0.8 cm to 1.2 cm.

*Color.*—Immature: RHS 155B and faintly tinged with RHS 145D. Mature: RHS 155B and tinged with RHS 145D and RHS 163D; occasionally marked with streaks of RHS 137C. Oldest stems: RHS 163D and RHS 195D and occasionally marked with RHS 137C.

*Shape and appearance.*—Columnar cylindrical and upright.

*Aspect.*—Vertical and upright.

*Strength.*—Sturdy and somewhat flexible.

*Axillary buds.*—Shape: Elliptic, flat to convex. Length: 0.3 cm. Width: 0.2 cm. Color: RHS 56B to RHS 56D.

Leaves:

*Arrangement.*—Alternate and simple; the leaves are arranged in a spiral along the stem; the leaf blade folds upward along the midrib.

*Quantity of leaves per stem.*—9.

*Immature leaf* (*newly expanded leaf*).—Color: Upper surface: Base color is between RHS 147A and RHS 146A with areas of RHS 189A which follow the primary veins; the leaf blade is variably marked with small RHS 144D coalescing spots and blotches; areas adjacent to the primary veins and midrib are RHS 144D and areas adjacent to the midrib are also variably tinged with RHS 53B to RHS 53C. Lower surface: Base color is RHS 147A and has an overall cast of RHS 50B to RHS 50C; the upper surface patterns and markings are visible through to the lower surface of the leaf; the leaf blade is marked with small coalescing RHS 50B to RHS 50C spots; the areas adjacent to the primary veins and midrib are between RHS 50B and RHS 50C.

*Mature leaf.*—Color: Upper surface: Base color is RHS 147A to RHS 147B with areas of RHS 189A which follow the primary veins; the leaf blade is variably marked with small coalescing spots and blotches between RHS 144D and RHS 158A; the areas adjacent to the primary veins and midrib are between RHS 144D and RHS 158A; the areas adjacent to the midrib are also variably tinged with RHS 46D. Lower surface: Base color is RHS 147A and has an overall cast of RHS 181C and RHS 50C; the upper surface patterns and markings are visible through to the lower surface of the leaf; the leaf blade is marked with small coalescing RHS 160D with between RHS 50C and RHS 50D spots; areas adjacent to the primary veins and the midrib are RHS 50C.

*Length.*—7.9 cm to 9.5 cm.

*Width.*—Flattened: 4.9 cm to 6.0 cm. Not flattened: 4.0 cm to 5.5 cm.

*Shape.*—Ovate.

*Apex.*—Acuminate to cuspidate.

*Base.*—Obtuse to slightly cordate.

*Margin.*—Smooth, entire and mostly flat with some broad undulations.

*Texture.*—Upper surface: Smooth; new leaves are shiny while mature leaves are glossy; Lower Surface: Smooth and glossy to dull; the leaf blade is convex between the main veins and somewhat puckered along the midrib resulting in a textured appearance.

*Pubescence.*—Absent.

*Venation pattern.*—Pinnate and radiating outward from the midrib in a herringbone arrangement.

Venation color. —Immature leaf (newly expanded leaf): Upper surface: Primary veins: RHS 54B. Midrib: RHS 53B to RHS 53C. Lower surface: Primary veins: RHS 50C. Midrib: Between RS 50C and RHS 50D. Mature leaf: Upper surface: Primary veins: RHS 158A tinged with RHS 54C. Midrib: RHS 46A tinged with RHS 46D. Lower surface: Primary veins: RHS 50C. Midrib: RHS 50D.

Petioles:

*Aspect.*—Vertical and upright when newly expanded and becoming curved outward to about 30 degrees to 45 degrees with maturity.

*Length.*—5.0 cm.

*Width* (*not flattened*).—0.6 cm.

*Diameter.*—Distal: 0.22 cm. Proximal (petiole and petiole sheath clasps the stem proximally): Flattened: 2.2 cm. Not flattened: 0.80 cm.

*Color.*—Distal (between the top of the wing and the base of the leaf): RHS 56A to RHS 56B and flushed with RHS 54B. Proximal: RHS 56C to RHS 56D. Areas adjacent to the stem: RHS 56D.

Wing:

*Length.*—4.4 cm.

*Diameter.*—Mid-point: 0.6 cm. Base: 0.8 cm. Depth: 0.5 cm.

*Color.*—Inside: RHS 56D and flushed with RHS 56A. Outside: RHS 56C to RHS 56D at the proximal end and RHS 56D flushed with RHS 54B at the distal end. Area adjacent to the stem: RHS 56D.

Cataphylls:

*Length.*—3.2 cm.

*Width.*—1.0 cm.

*Shape.*—Linear to lanceolate, keeled and translucent.

*Texture.*—Inner surface is smooth and shiny while outer surface is glossy.

*Apex.*—Cuspidate.

*Base.*—Clasps the peduncle or stem.

*Color.*—Inner and outer surfaces: Translucent; RHS 155D at the proximal end, RHS 56C to RHS 56D at the distal end and becoming RHS 54B near the apex.

Inflorescence:

*Appearance.*—Hooded spathes surrounding a columnar spadix are borne atop an upright peduncle;

monoecious; the spadix is a central column of sessile, simple male and female flowers separated into two zones; the male flowers occupy the upper two-thirds of the spadix while the female flowers occupy the lower one-third of the spadix.

*Quantity of inflorescences per stem.*—About 1.

*Quantity of inflorescences per plant.*—About 2.

*Aspect.*—Upright.

*Height* (*from base of peduncle to tip of spathe*).—6.3 cm.

*Diameter/width.*—1.0 cm.

*Flowering habit.*—Seasonal; the natural flowering season is summer and fall as observed in Apopka, Fla.; the flowers are persistent.

*Fragrance.*—Absent.

*Ratio of inflorescence to opening.*—About 1 new flower every 21 days.

*Peduncle.*—Length: 3.6 cm. Diameter: 0.28 cm. Aspect: Upright and curved. Strength: Sturdy and flexible. Color: Distal: RHS 158D tinged with RHS 56C. Proximal: RHS 158D.

Spathe:

*Appearance.*—Simple, hooded, cupped and enclosing the spadix.

*Aspect.*—Upright.

*Shape.*—Elliptic.

*Apex.*—Acute.

*Margin.*—Entire.

*Texture.*—Both, front and rear sides: Smooth and glossy.

*Size.*—Length: 3.3 cm. Width: 1.0 cm (not flattened) and 2.5 cm (flattened).

*Color* (*fully opened*).—Front side: RHS 56D at the proximal end and RHS 56A at the distal end. Rear side: RHS N155B at the proximal end and RHS 56B at the distal end.

Spadix:

*Appearance and shape.*—Columnar.

*Aspect.*—Upright.

*Size.*—Length: 1.5 cm. Diameter of the female zone: 0.55 cm. Diameter of the male zone: 0.4 cm. Length of the female zone: 0.4 cm. Length of the male zone: 0.11 cm.

*Apex.*—Obtuse.

*Base.*—Obtuse.

*Margin.*—Pebbled.

Flowers:

*Type.*—Simple.

*Quantity of female flowers per spadix.*—12.

*Quantity of male flowers per spadix.*—90.

*Shape of female.*—Ovate.

*Shape of male.*—Obovate, inverted triangle.

*Size.*—Female width: 0.15 cm. Male width: 0.10 cm. Female height: 0.15 cm. Male height: 0.12 cm.

Reproductive organs:

*Stigma color.*—RHS 158D.

*Ovary color.*—RHS 144D.

*Anther color.*—RHS 158C.

Fruit and seed set: None observed.

Disease and insect resistance: Typical of *Aglaonema* species; no particular susceptibility or resistance to pests or diseases noted.

COMPARISON WITH KNOWN VARIETIES

'TWYAG0054' differs from the commercial variety 'TWYAG003' (U.S. Plant Pat. No. 17,673) in 'TWYAG054' has a shorter and narrower growth habit than 'TWYAG003'. In addition, the leaves of 'TWYAG0054' are a different shade of green and have considerably fewer spots and blotches than the leaves of 'TWYAG0003'.

I claim:

1. A new and distinct cultivar of *Aglaonema* plant as shown and described herein.

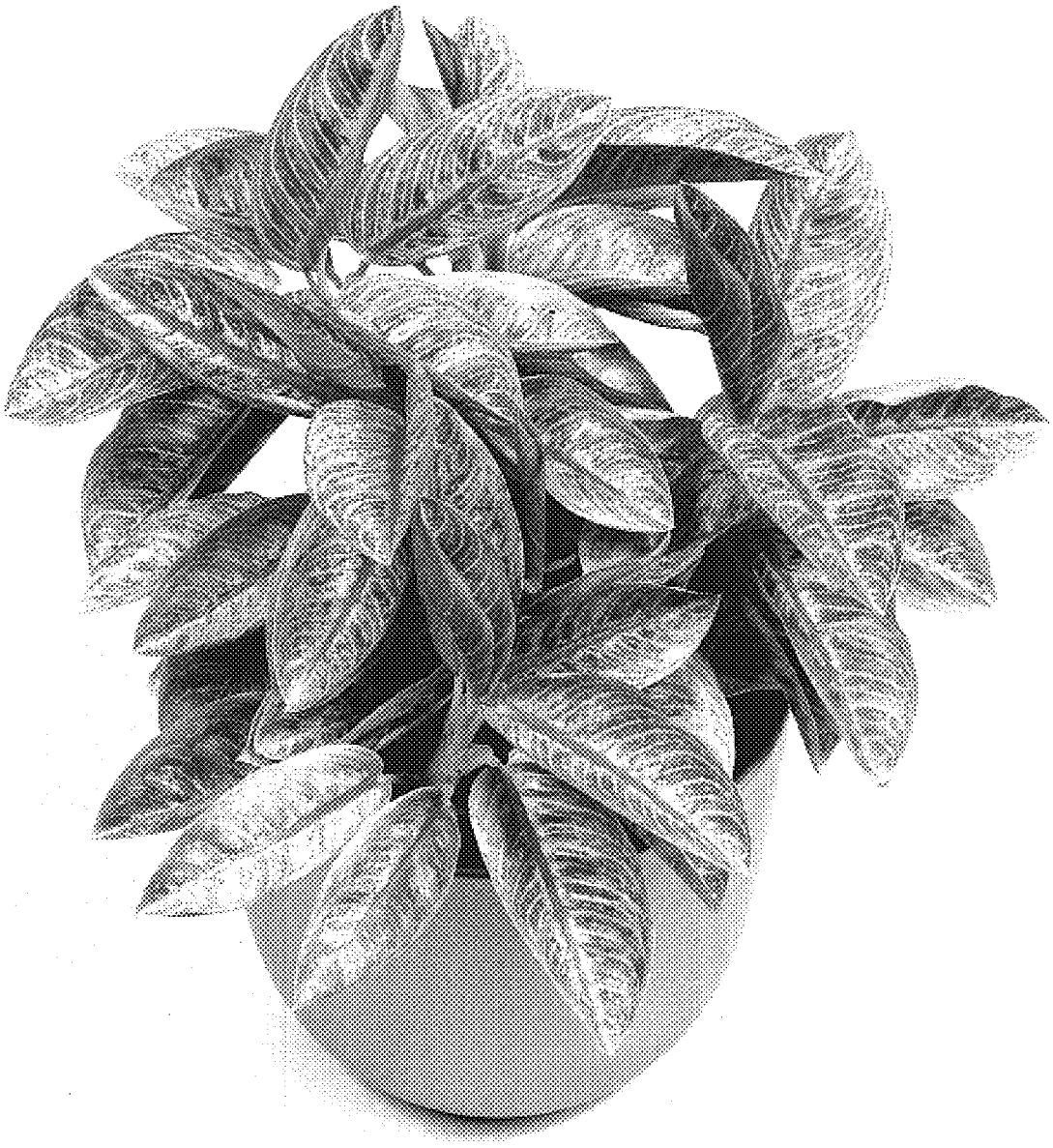

* * * * *